United States Patent
Hacker et al.

(10) Patent No.: US 8,095,196 B2
(45) Date of Patent: Jan. 10, 2012

(54) MICROSENSOR NEEDLE FOR PH MEASUREMENT IN TISSUE

(75) Inventors: Thomas G. Hacker, Anaheim, CA (US); Tetsuro Kawanishi, Tokyo (JP)

(73) Assignee: Terumo Cardiovascular Systems, Ann Arbor, MI (US)

( * ) Notice: Subject to any disclaimer, the term of this patent is extended or adjusted under 35 U.S.C. 154(b) by 1419 days.

(21) Appl. No.: 11/642,036

(22) Filed: Dec. 19, 2006

(65) Prior Publication Data

US 2008/0146902 A1    Jun. 19, 2008

(51) Int. Cl.
*A61B 5/1459* (2006.01)
*A61B 5/00* (2006.01)
*G02B 6/00* (2006.01)
*G01N 33/50* (2006.01)

(52) U.S. Cl. ............ 600/342; 600/310; 385/12; 436/68

(58) Field of Classification Search ................... 600/324, 600/325, 339, 342, 310; 436/68
See application file for complete search history.

(56) References Cited

U.S. PATENT DOCUMENTS

| 4,548,907 | A | | 10/1985 | Seitz et al. | |
|---|---|---|---|---|---|
| 4,560,248 | A | * | 12/1985 | Cramp et al. | 385/12 |
| 4,622,974 | A | * | 11/1986 | Coleman et al. | 600/342 |
| 4,798,738 | A | | 1/1989 | Yafuso et al. | |
| 5,273,716 | A | | 12/1993 | Northrup et al. | |
| 5,277,872 | A | | 1/1994 | Bankert et al. | |
| 5,353,792 | A | * | 10/1994 | Lubbers et al. | 600/311 |
| 5,596,988 | A | * | 1/1997 | Markle et al. | 600/353 |
| 6,009,339 | A | | 12/1999 | Bentsen et al. | |
| 6,058,321 | A | * | 5/2000 | Swayze et al. | 600/310 |
| 6,370,406 | B1 | * | 4/2002 | Wach et al. | 600/310 |
| 6,567,679 | B1 | | 5/2003 | Khuri et al. | |
| 6,584,335 | B1 | * | 6/2003 | Haar et al. | 600/322 |
| 6,600,941 | B1 | | 7/2003 | Khuri | |
| 2002/0169426 | A1 | * | 11/2002 | Takagi | 604/272 |
| 2005/0113658 | A1 | * | 5/2005 | Jacobson et al. | 600/316 |

OTHER PUBLICATIONS

Mitsubishi Rayon Co., Ltd., Eska Optical Fiber Division, *Specification Sheet—SH-2001, Super Eska Polyethylene Jacketed Optical Fiber Cord, High Performance Plastic Optical Fiber*, Jul. 2001, pp. 1-3.

* cited by examiner

*Primary Examiner* — Eric Winakur
*Assistant Examiner* — Chu Chuan (JJ) Liu
(74) *Attorney, Agent, or Firm* — McMillan, Sobanski & Todd; Gael Diane Tisack, Esq.; Darryl Newell (57) ABSTRACT

A sensor probe for in-situ measurement of pH in a human tissue (e.g., cardiovascular) environment comprises a hollow needle having a tip and a back end. The tip is insertable into the tissue. An optic cable comprises a light conduit surrounded by a cladding. A first end of the light conduit is inserted from the back end of the needle and extends to within a predetermined distance of the tip to define a cavity within the tip. A porous dye layer is contained within the cavity, wherein the dye layer has a response to excitation light delivered through the light conduit that varies according to the pH of the tissue environment. An overcoat layer is deposited on the dye layer, wherein the overcoat layer is ionically permeable and substantially opaque at a light wavelength corresponding to the variable response of the dye layer.

18 Claims, 6 Drawing Sheets

MICROSENSOR NEEDLE FOR PH MEASUREMENT IN TISSUE

CROSS REFERENCE TO RELATED APPLICATIONS

Not Applicable.

STATEMENT REGARDING FEDERALLY SPONSORED RESEARCH

Not Applicable.

BACKGROUND OF THE INVENTION

The present invention relates in general to monitoring pH levels in human tissue (such as ischemia in cardiac tissue), and, more specifically, to a microsensor needle adapted to in-situ pH measurement in human tissue.

It is known in the field of cardiac surgery that the pH of heart tissue can be indicative of conditions in which the tissue receives insufficient oxygen. If the heart does not have sufficient oxygen, ischemia can occur. Measurement of the pH can be performed using an optical sensor having a material which fluoresces in accordance with the pH of the environment into which the florescent material is immersed (e.g., blood or tissue). For example, U.S. Pat. No. 4,798,783 to Yafuso et al discloses a micro pH sensor providing a dye material at the end of an optical fiber. Excitation light is transmitted down the optical fiber to the dye material which is selected to either fluoresce or to specifically absorb the excitation light. The ionic content of the fluidic environment into which the dye material is immersed affects the florescent or absorbing properties of the material. Light from the dye material travels back up the optical fiber to a detector for characterizing the pH. Since the excitation properties of the material also depend upon the temperature, a thermistor or other temperature sensor is typically included in the sensor probe. The emitted/returned light and the temperature are utilized by conventional algorithms to determine a pH value.

Prior art micro-sensors have typically employed glass probes. Such probes are relatively expensive and, even though they are smaller than some other types of probes, are still sufficiently large to require the creation of a passage through heart tissue having a size that can cause cellular damage. Moreover, existing probe designs have been difficult to sterilize and have had a relatively short shelf life. There is a need in the art to provide a device and method for manufacturing the device which is capable of measuring pH of tissue during cardiovascular surgery or other interrogation of human tissue that is cost effective, has a relatively long shelf life, is easy to use and sterilize, and reduces damage to tissue. Moreover, there is a need to provide a microsensor that is easily placed in a wide variety of tissue types and locations.

SUMMARY OF THE INVENTION

The invention utilizes a needle to encase the end of a light conduit and to retain a dye layer and an overcoat layer in a manner that achieves low manufacturing cost while obtaining accurate pH measurements from a very small device which is easy to use and sterilize, easy to insert or attach to a patient, and which has a long shelf life.

In one aspect of the invention, a sensor probe for in-situ measurement of pH in a human tissue environment comprises a hollow needle having a tip and a back end. The tip is insertable through tissue into the human tissue environment. An optic cable comprises a light conduit surrounded by a cladding. A first end of the light conduit not covered by the cladding is inserted from the back end of the needle and extends to within a predetermined distance of the tip to define a cavity within the tip. A porous dye layer is contained within the cavity adjacent to the first end of the light conduit, wherein the dye layer has a response to excitation light delivered through the light conduit that varies according to the pH of the human tissue environment. An overcoat layer is deposited on the dye layer, wherein the overcoat layer is ionically permeable and substantially opaque at a light wavelength corresponding to the variable response of the dye layer.

DETAILED DESCRIPTION OF PREFERRED EMBODIMENTS

Figures 1, 2:
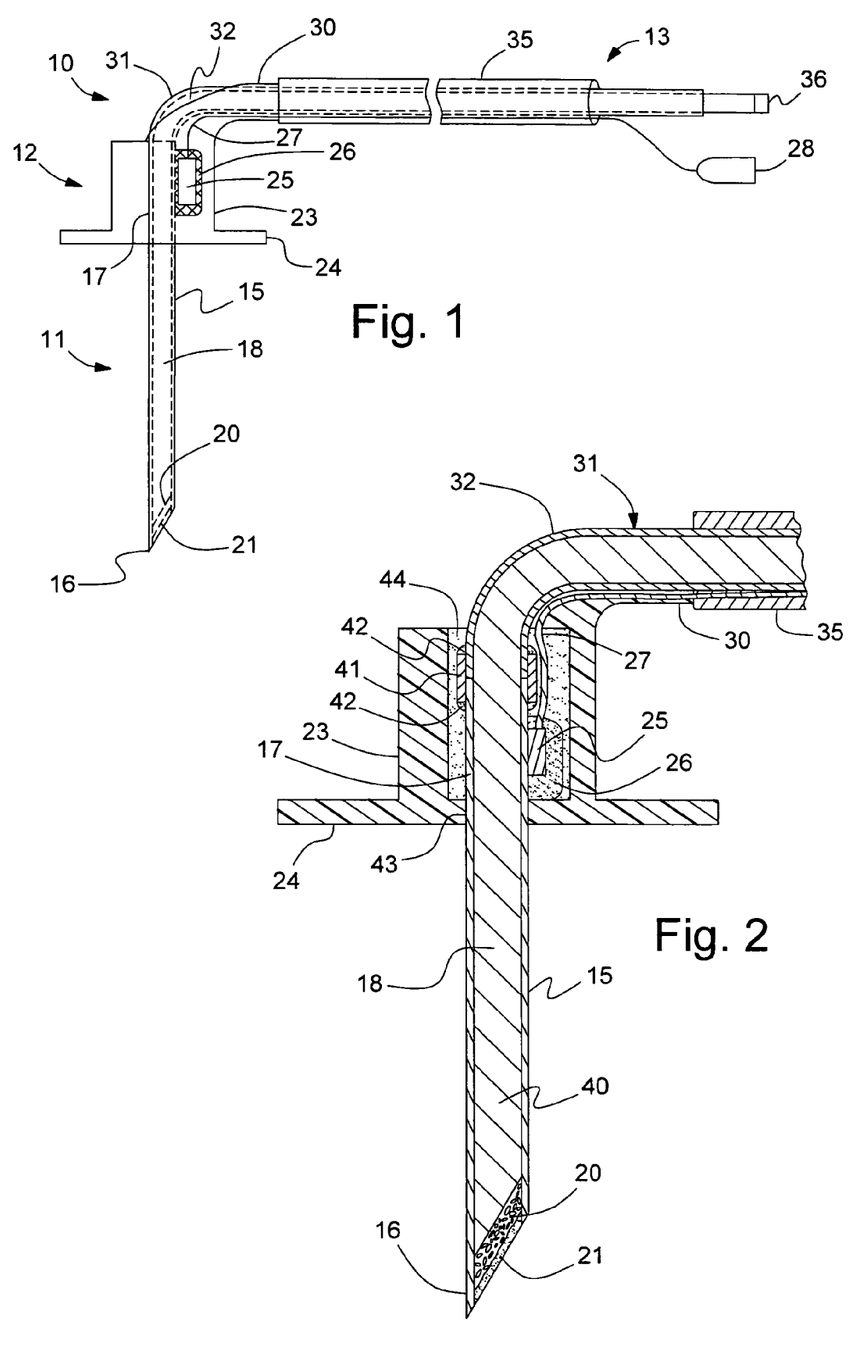
FIG. 1 is a side view of a sensor probe and connector cables of the present invention.
FIG. 2 is a cross-sectional view of the sensor probe.

Referring to FIG. 1, a sensor probe assembly 10 includes a needle section 11, a housing section 12, and a cable bundle section 13. Needle section 11 includes a hollow, cylindrical needle 15 having a tip 16 and a backend 17 which is retained in housing section 12. Needle 15 is preferably comprised of stainless steel. Needle tip 16 has a planar profile that is slanted at a predetermined angle with respect to a longitudinal axis of needle 15. A first end of a light conduit 18 of an optic cable is contained within needle 15 and is spaced a predetermined distance from tip 16 in order to create a cavity for containing a porous dye layer 20 and an overcoat layer 21. Housing section 12 includes a main body 23 and a stitch-on disk 24. Main body 23 receives backend 17 of needle 15 and secures it therein. A thermistor 25 is attached to the backend 17 of needle 15 by a heat conductive adhesive 26. A thermistor such as the A070M-SC30BF10A from Thermometrics, Inc., can be employed. A signal wire 27 connects thermistor 25 to an electrical connector 28 in wire bundle section 13. Main body 23 has an integral support arm 30 for receiving optic cable 31 so that optic cable 31 can be kept out of the way during use. Optic cable 31 includes a cladding 32 which is removed at the first end where light conduit 18 is received by needle 15. A plastic optic fiber such as the SH-2001-J fiber from Mitsubishi Rayon Company Ltd may be used.

Cable bundle section 13 includes an outer jacket 35 for retaining thermistor signal wire 27 together with the intermediate and second end portions of optical cable 31. The second end of optic cable 31 includes an optical connector 36 for joining with a control module having a light emitter and a light detector for interfacing with optic cable 31 and having an electronic controller for receiving signals from the thermistor and for performing the known operations for calculating a pH value.

The sensor probe assembly 10 is shown in greater detail in cross-section in FIG. 2. A first end 40 of the light conduit or fiber is retained inside needle 15 where the cladding has been removed. The end of the cladding 32 abuts the back end 17 of needle 15. A cylindrical ferrule 41 is placed over the joint between cladding 32 and needle end 17 and is attached by epoxy 42 for holding ferrule 41 in place. Ferrule 41 is preferably made of stainless steel.

Thermistor 25 thermally contacts needle 15 and is held in place by a thermally-conductive adhesive 26 (such as T7110 from Epoxy Technology, Inc.). In order to retain the needle and thermistor assembly in housing 23, after the thermistor is attached to the needle then tip 16 of needle 15 is pushed through an aperture 43 in housing main body 23 and then the backend 17 of the needle together with the thermistor, its wiring, and the ferrule are fixed in place by injecting epoxy 44 to fill the remaining space in the interior of main body 23.

Figure 3:
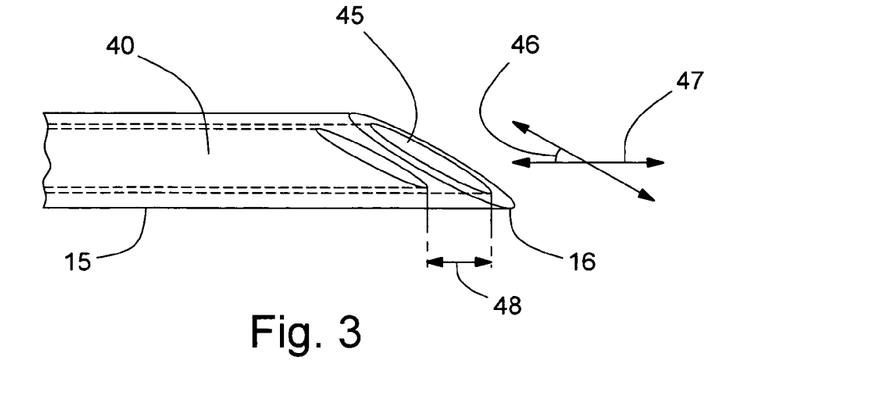
FIG. 3 is a perspective view of the probe tip.

Referring to FIG. 3, first end 40 of light conduit 18 is located with respect to tip 16 of needle 15 in order to create a cavity 45 as follows. Tip 16 is cut to have a planar profile that is slanted at a predetermined angle 46 with respect to a longitudinal axis 47 of the needle. Likewise, light conduit 40 has an end face that is slanted to be substantially parallel with the planar profile of tip 16. Upon insertion of light conduit 18 through the backside of needle 17, the insertion length and orientation are controlled in order to maintain a gap 48 between the end of light conduit 40 and tip 16, thereby creating cavity 45 of a predetermined size. In a preferred embodiment, angle 46 is about 30°. The most preferred needle size is about 22 gauge and the stainless steel needle preferably has a length of about 10 mm. Preferably, the length of gap 48 is equal to about 0.2 mm resulting in a slanted cavity having a longitudinal thickness of 0.2 mm. In addition to facilitating entry of the needle into and through human tissue, the slanted tip allows for a greater contact surface area between the dye and overcoat layers and the cardiac environment, thereby providing an increased sensitivity of detection.

Figure 4:
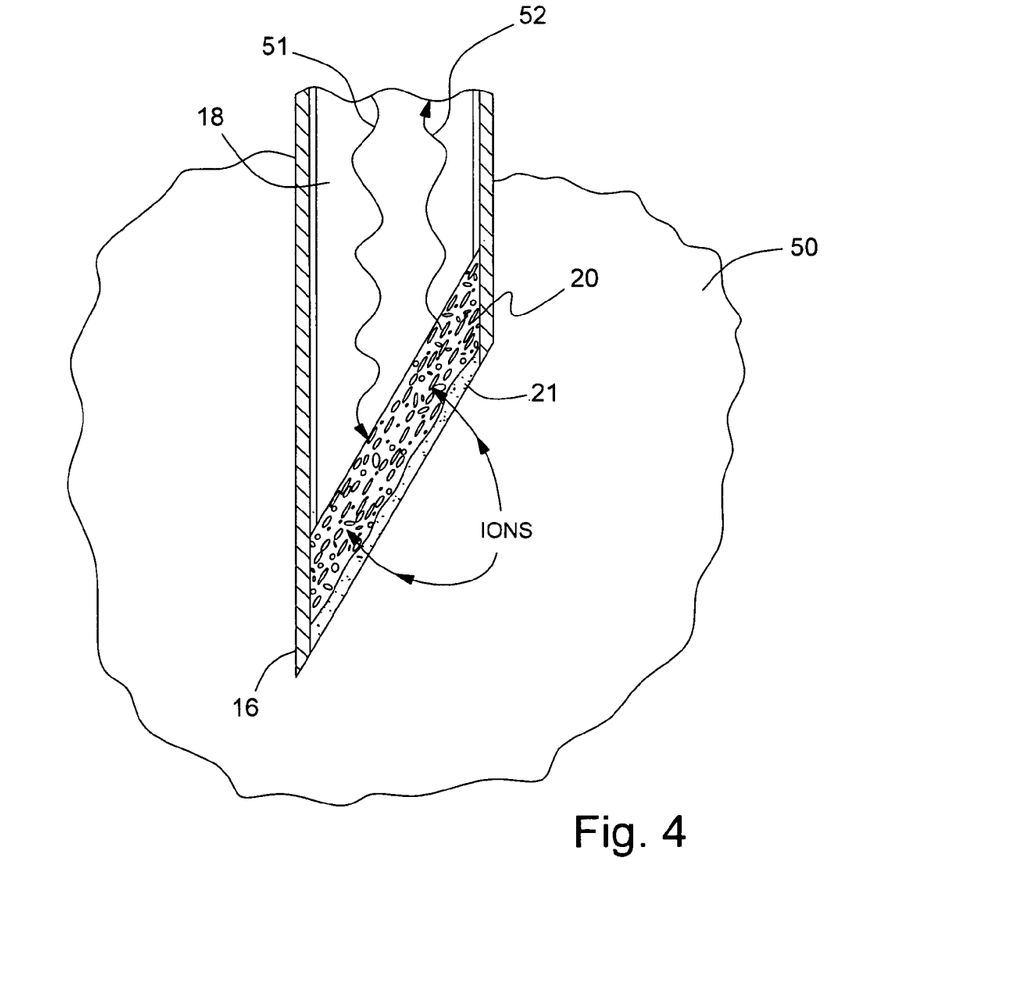
FIG. 4 is a cross-sectional view of the probe tip in greater detail.

FIG. 4 shows needle tip 16 inserted into a cardiovascular environment 50. When an acidic pH associated with ischemia is present, ions from cardiac environment 50 migrate through overcoat layer 21 into dye layer 20. Incident excitation light 51 illuminates dye layer 20 via light conduit 18. After the excitation light is turned off, a response in the form of emitted light from dye layer 20 returns up through light conduit 18 in the form of emitted light 52. In a preferred embodiment, the intensity of emitted radiation 52, along with the measured temperature are used to characterize pH in a known manner. Porous dye layer 20 can comprise any known material such as an ATPS-cellulose material. Overcoat layer 21 deposited on the dye layer is ionically permeable and is substantially opaque at light wavelengths corresponding to the excitation light and the emitted light of dye layer 20. In one preferred embodiment, excitation light is provided by lasers at 410 nm and 470 nm and the emitted light is at a wavelength of 520 nm, and overcoat layer 21 is substantially opaque at all three frequencies so that ambient light does not interfere with the sensor.

Figure 5:
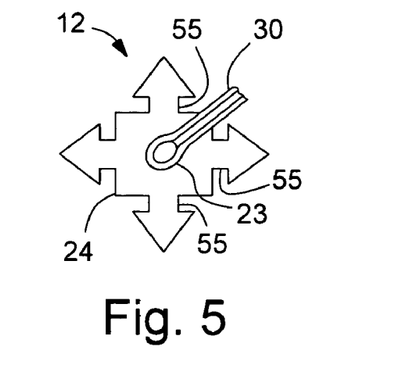
FIG. 5 is a top view showing a first embodiment of a stitch-on disk.
Figure 6:
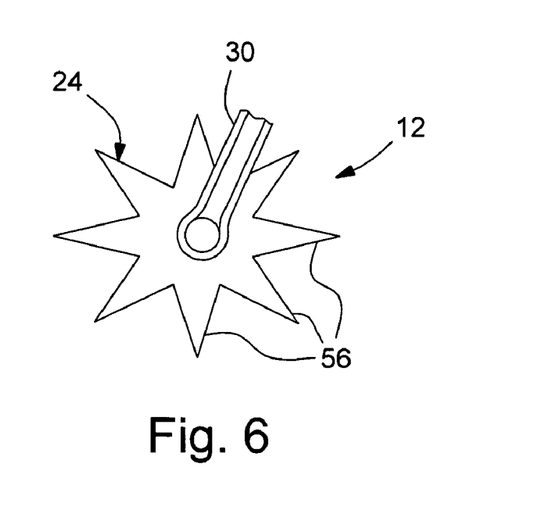
FIG. 6 is a top view showing a second embodiment of a stitch-on disk.

FIG. 5 shows a top view of housing section 12 illustrating one embodiment for a stitch-on disk 24 to facilitate suturing of the sensor probe in place after inserting the needle tip into tissue of interest. In particular, narrow portions 55 are provided so that sutures can be looped around the narrow portions to securely retain the sensor probe in place. Likewise, in FIG. 6 a plurality of star-shaped projections 56 perform the same function.

Figures 11, 12, 13:
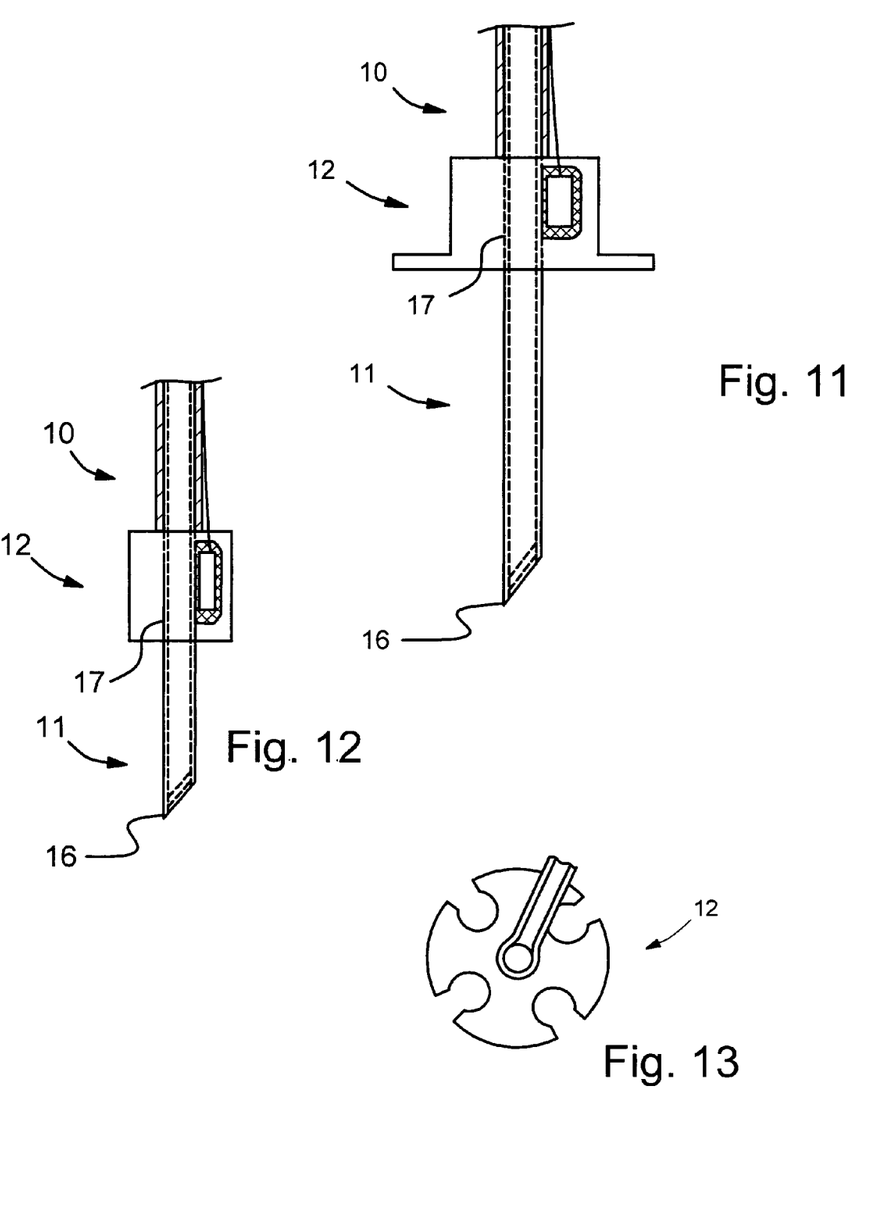
FIG. 11 is a side view of a sensor probe in a straight configuration.
FIG. 12 is a side view of a sensor probe having a narrow housing adapted to be insertable into a body.
FIG. 13 is a top view showing a third embodiment of a stitch-on disk.

The right angle orientation for handling the optic cable and cable bundle shown in FIGS. 1 and 2 is especially adapted for certain types of cardiovascular surgery. For other monitoring applications, a straight device as shown in FIG. 11 is more desirable. The housing in FIG. 11 retains a stitch-on disk but the support for the cable bundle is coaxial with the needle section.

For other tissue monitoring applications, it is desirable to provide a sensor probe that is insertable through the skin or other intervening tissue to reach the tissue of interest. FIG. 12 shows another embodiment having a shortened needle section and a reduced-diameter housing section without a stitch-on disk, whereby the sensor probe is easily insertable into a body of a patient.

FIG. 13 shows yet another embodiment for providing a stitch-on support disk with indentations to be used for suturing.

Figure 7:
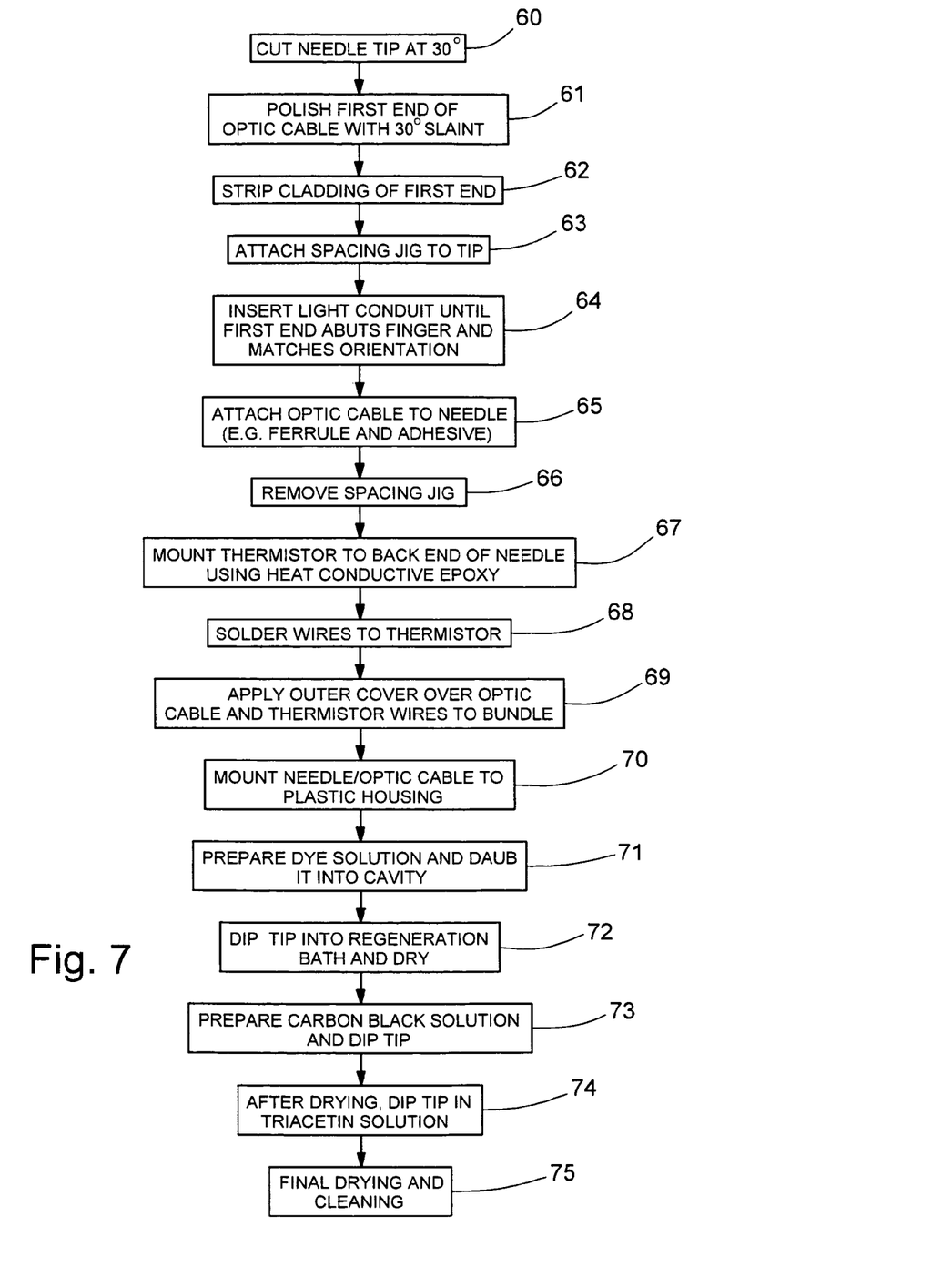
FIG. 7 is a flowchart showing a preferred manufacturing method for making the sensor probe of the present invention.
Figure 8:
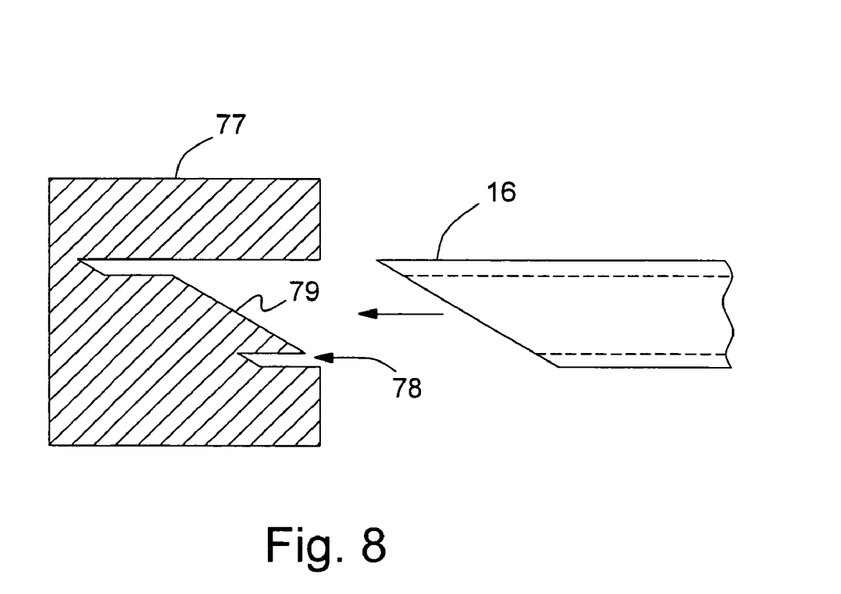
FIG. 8 illustrates the use of a spacing jig for receiving the needle tip.
Figure 9:
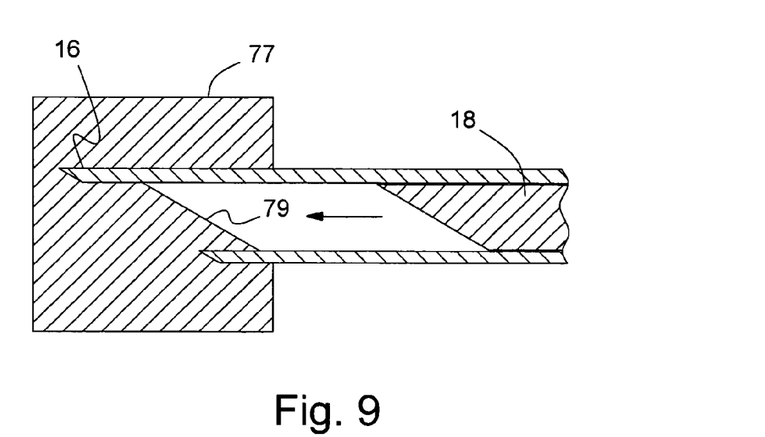
FIG. 9 illustrates the insertion of an optic cable through the needle to the spacing jig for orienting the optic cable with respect to the needle.

Turning now to a preferred low cost manufacturing method for the sensor probe of the present invention in FIG. 7, a hollow, cylindrical, stainless steel needle is cut at its tip at an angle of 30° in step 60. In step 61, the first end of an optic cable is polished at an angle (e.g., in a polishing machine) to provide a 30° slant to the end of the optic cable. After polishing the end to the desired shape, cladding is stripped off the first end of the optic cable in step 62. The stripped end of the optic cable may have a length of about 10 mm, for example. In order to obtain a desired gap and proper orientation of the light conduit inside the needle, a spacing jig 77 as shown in FIG. 8 is employed. A receptacle 78 in spacing jig 77 is shaped as a cylindrical tunnel for receiving needle tip 16. A finger 79 is adapted to be received within the interior of needle tip 16 and to extend a predetermined distance into the interior. Finger 79 has a slanted surface matching the slant of the end of the light conduit. FIG. 9 shows needle tip 16 inserted all the way into spacing jig 77 and illustrates the insertion of light conduit 18. Light conduit 18 advances through the needle until it abuts the slanted face of finger 79.

Returning to FIG. 7, after the spacing jig is attached to the needle tip in step 63 and the light conduit is advanced through the needle until the first end abuts the finger and matches its orientation in step 64, the optic cable and needle are fixed together in step 65. In a preferred embodiment, a ferrule is slid over the needle and optic cable to bridge the back end of the needle and the cladding of the optical cable and then adhesive is applied around the ferrule. The spacing jig is removed in step 66 and then the thermistor is mounted to the backend of the needle using a heat conductive epoxy in step 67. In step 68, the signal wires of the thermistor are soldered to the thermistor and then the wires are bundled with the optic cable in step 69 by applying an outer cover over the bundle.

The needle assembly is mounted to the plastic housing in step 70. In a preferred embodiment, a fixture is provided for holding the needle assembly in the proper position within the plastic housing while epoxy is injected into the interior of the plastic housing. A dye solution is prepared in step 71 and then daubed into the cavity inside the needle tip. The tip is then dipped into a regeneration bath and dried in step 72. In step 73, a carbon black solution is prepared and the tip with the dye layer already formed is dipped into the carbon black solution. After drying, the needle tip is dipped in a triacetin solution 74. Final drying and cleaning are performed in step 75 and then the sensor probe may be packaged, stored, and distributed for use.

Figure 10:
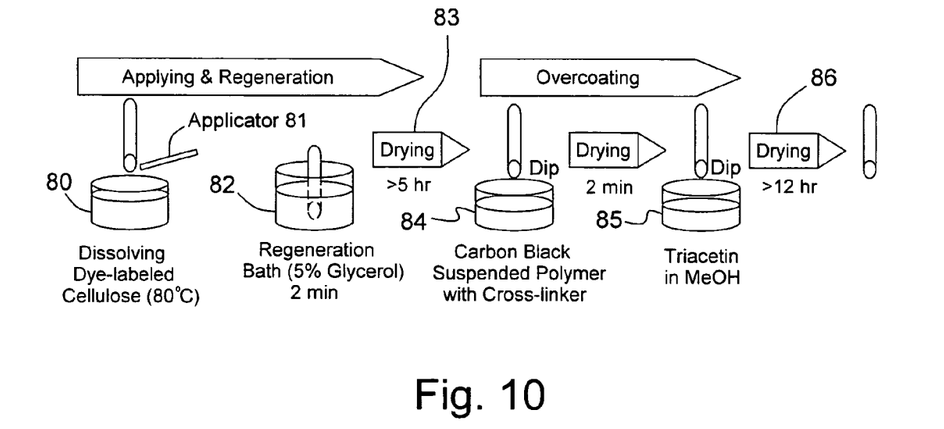
FIG. 10 illustrates a preferred method for applying the dye layer and overcoat layer to the cavity in the needle tip.

FIG. 10 shows the formation of the chemical layers in greater detail. As an initial step, the needle tip and optical fiber ends are washed with ethanol and well dried. An HTPS-cellulose solution of the type known in the art is prepared in a vessel 80. For example, a dye-labeled cellulose solid may be obtained by 1) mixing acetoxypyrenetrisulfonic acid trichloride with acetone, a sodium carbonate buffer, and aminoethylcellulose powder, 2) adding to salt water and decomposing by heating, and 3) filtering out the resulting solids. The solid is then mixed with 4-methylmorpholine-N-oxide to provide an HTPS-cellulose solution. An applicator 81 such as a thin plastic rod is dipped into the cellulose solution and touched to the tip of the needle. The solution covers the end of the optical fiber and then the needle tip is immersed into a 5% glycerol solution for 2 minutes as shown at 82. Thereafter, the resulting dye layer is dried at room temperature for five hours as shown at 83.

In order to create the overcoat layer, a suspended-polymer carbon black solution is placed in a vessel 84. The carbon black solution may be obtained by mixing into deionized water dextran (e.g., Sigma D5376) and carbon black (e.g., a blend of Marasperse CBOS-4 and Monarch-700). The resulting solution is insonified and then mixed with cross-link solution comprising 1,6-hexyldiamine and ethyleneglycol diglycidylether. The needle tip is dipped into the cross-linker solution for about 2 minutes and then dipped into a triacetin solution in a vessel 85 to provide a hygroscopic surface. The sensor is then dried at room temperature for at least 12 hours as shown at 86. Thereafter, the sensor tip may be immersed in a phosphate buffer with a pH of about 7.0 for ten hours and then dried again.

What is claimed is:

1. A sensor probe for in-situ measurement of pH in a human tissue environment comprising:
   a hollow needle having a tip and a back end, the tip being insertable through tissue into the human tissue environment;
   an optic cable comprising a light conduit surrounded by a cladding, wherein a first end of the light conduit not covered by the cladding has an outer diameter substantially conforming to the inner diameter of the hollow needle, is inserted from the back end of the needle, and extends to within a predetermined distance of the tip to define a cavity within the tip, wherein the optic cable is fixed to the hollow needle with the cladding abutting the back end of the needle;
   a porous dye layer within the cavity adjacent to the first end of the light conduit, wherein the dye layer has a response to excitation light delivered through the light conduit that varies according to the pH of the human tissue environment; and
   an overcoat layer deposited on the dye layer, wherein the overcoat layer is ionically permeable and substantially opaque at a light wavelength corresponding to the variable response of the dye layer.

2. The sensor probe of claim 1 wherein the hollow needle is comprised of stainless steel and is cylindrically shaped.

3. The sensor probe of claim 1 wherein the hollow needle is cylindrically shaped and wherein the tip has a planar profile that is slanted at a predetermined angle with respect to a longitudinal axis of the needle.

4. The sensor probe of claim 3 wherein the first end of the light conduit is slanted to be substantially parallel with the planar profile of the needle tip.

5. The sensor probe of claim 3 wherein the predetermined angle is about 30°.

6. The sensor probe of claim 1 wherein the porous dye layer fluoresces in response to the excitation light.

7. The sensor probe of claim 1 wherein the overcoat layer is comprised of carbon black.

8. The sensor probe of claim 1 further comprising a plastic housing fixedly mounting the back end of the needle and a portion of the optic cable including the cladding.

9. The sensor probe of claim 8 wherein the plastic housing includes a main body with a stitch-on disk extending from the main body.

10. The sensor probe of claim 8 further comprising a thermistor mounted to the plastic housing and thermally coupled to the hollow needle.

11. A method of manufacturing a sensor probe for in-situ measurement of pH in a human tissue environment, comprising the steps of: preparing a hollow needle having a slanted tip and a back end, the slanted tip being insertable through tissue into the human tissue environment; preparing a cladded optic cable by removing the cladding from a first end of a light conduit within the optic cable where the light conduit not covered by the cladding has an outer diameter substantially conforming to the inner diameter of the hollow needle; attaching a spacing jig onto the slanted tip of the hollow needle wherein the spacing jig has a finger extending from a base, the spacing jig being attached to the needle so that the slanted tip contacts the based and the finger extends into the interior of the hollow needle to define a cavity; inserting the first end of the light conduit through the back end of the hollow needle to abut the finger of the spacing jig; fixing the optic cable to the hollow needle with the cladding abutting the back end of the needle; removing the spacing jig from the hollow needle to expose the cavity; applying a porous dye layer within the cavity adjacent to the first end of the light conduit, wherein the dye layer has a response to excitation light delivered through the light conduit that varies according to the pH of the human tissue environment; and applying an overcoat layer on the dye layer, wherein the overcoat layer is ionically permeable and substantially opaque at a light wavelength corresponding to the variable response of the dye layer.

12. The method of claim 11 further comprising the step of:
   forming the first end of the light conduit to be slanted at about the same angle as the slanted tip of the hollow needle;
   wherein the base of the spacing jig and the finger of the spacing jig have surfaces slanted at about the same angle as the slanted tip of the hollow needle, and wherein the slanted profiles of the tip of the needle and the first end of the light conduit become substantially parallel when the first end of the light conduit abuts the finger of the spacing jig.

13. The method of claim 11 wherein the step of fixing the optic cable to the hollow needle is comprised of gluing a ferrule over the optic cable and the hollow needle.

14. The method of claim 11 further comprising the steps of:
   mounting a thermistor in thermal communication with the hollow needle;
   connecting wires to the thermistor; and
   bundling the wires with the optic cable.

15. The method of claim 14 further comprising the step of:
mounting the hollow needle and thermistor to a plastic housing that includes a main body with a stitch-on disk extending from the main body.

16. The method of claim 11 further comprising the step of:
mounting the back end of the hollow needle to a plastic housing that includes a main body with a stitch-on disk extending from the main body.

17. The method of claim 11 wherein the step of applying a porous dye layer within the cavity comprises:
preparing a dye-labeled cellulose solution;
daubing the dye-labeled cellulose solution into the cavity;
immersing the slanted needle tip into a regeneration bath; and
drying the porous dye layer.

18. The method of claim 11 wherein the step of applying an overcoat layer on the dye layer comprises:
dipping the slanted needle tip into a carbon black solution;
after drying, dipping the slanted needle tip into a triacetin solution; and
drying the overcoat layer.

* * * * *